Dec. 11, 1956 T. E. MOTOSE Plant Pat. 1,537
ROSE PLANT
Filed Jan. 27, 1956
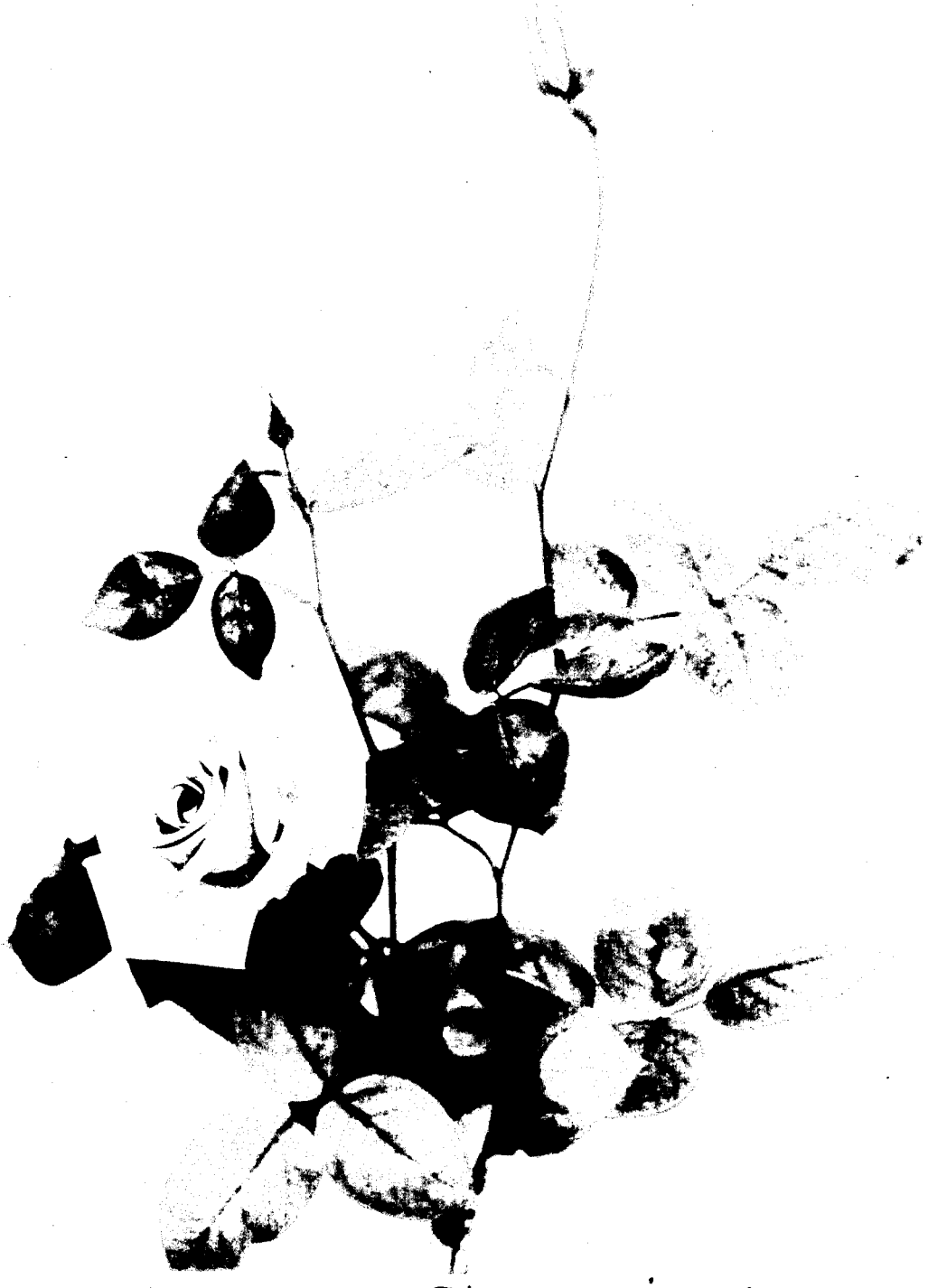
Discoverer-inventor
Thomas Edison Motose United States Patent Office Plant Pat. 1,537
Patented Dec. 11, 1956

1,537

ROSE PLANT

Thomas Edison Motose, Fairport, N. Y.

Application January 27, 1956, Serial No. 561,955

1 Claim. (Cl. 47—61)

This discovery or invention relates to a new and distinct variety of plant of the genus Rosa originating as a mutation of the variety known in commerce as Vierlanden (not patented).

The said sport or mutant was found by me on a Vierlanden bush grown personally by me in my experimental rose bed in Fairport, N. Y. I am the sole owner of both the parent bush and the sport.

Vierlanden, the parent variety, is a tall bush type rose plant of the hybrid-tea class, with abundant thorns and bearing deep salmon pink blooms which have a magenta overcast on the outer larger petals.

One of my Vierlanden bushes produced a sport possessing thorny cane and bearing clear rose pink blooms. I permitted this sport to remain and grow on the Vierlanden bush. Later I removed the branches bearing the regular Vierlanden blooms so that all the nourishments would go to the new sporting branch. As a result, the sport grew and produced many new branches, some very heavily thorned while others less thorned. I found among the medium and the heavily thorned branches, one smooth branch with one inconspicuous looking thorn or "prickle." I, then, removed and discarded one by one all the thorny branches until only the almost thornless one was left to receive all the nourishments from the old root-system. The present discovery or invention, the subject of this application, is the variety of rose plant produced asexually from the said almost thornless branch of the said thorned sport of Vierlanden.

DIFFERENTIATING CHARACTERISTICS

The new variety, the subject of this application, is distinguished from its parent Vierlanden on several major characteristics as shown in the following comparison:

(*a*)

*New variety.*—Rose Bengal (Plate No. 25/3 "Hort.") colored blooms without any magenta overcast; medium thick and medium size petals.

*Vierlanden.*—Very deep salmon pink colored blooms, with magenta overcast on the larger outer petals; thick and large petals.

Tests conducted in the experimental rose garden in Fairport, N. Y., show that the colors of the two roses are sufficiently different as to be distinguishable even at a distance of 150 or more feet in ordinary daylight by persons of normal eyesight.

(*b*)

*New variety.*—Large, long canes; about a dozen or less thorns on the lower parts of an average bush; as a general rule no thorns on the upper canes or upper parts of the bush; averaging one or less thorn on a branch.

*Vierlanden.*—Large, long canes; 50 to 100 thorns on an average branch.

The difference in the quantity of thorns on the two varieties is sufficiently great that an average person, blind-folded, can separate the new variety from Vierlanden by the sense of touch alone. (Tests conducted in the experimental garden in Fairport, N. Y.)

(*c*)

*New variety.*—Same texture and size of foliage as those on Vierlanden; same color of leaves as those of parent.

*Vierlanden.*—Leathery textured leaves; Spinach Green (Plate No. 5 "Ridg.") mature leaves; Light Greenish Yellow (Plate No. 5 "Ridg.") young leaves; ovoid and slightly pointed leaflets.

(*d*)

*New variety.*—Similar size bush (average specimen) and growth habit as those of Vierlanden.

*Vierlanden.*—Large, tall bush; strong, vigorous growth.

(*e*)

*New variety.*—A mixture of sweet *Rosa centifolia* and *Rosa damascena* fragrances, without the scent of tea.

*Vierlanden.*—A mixture of sweet *Rosa centifolia* and *Rosa damascena* fragrances, with an appreciable addition of tea scent.

Vierlanden is universally recognized as a distinct variety and is listed in authoritative publications, such as the fourth edition of "Modern Roses." The combination of the various characteristics possessed in common by Vierlanden and this new variety and the various characteristics not possessed by Vierlanden but possessed by this new variety makes this new variety different from Vierlanden and all other varieties.

Asexual reproductions of the said new variety by the usual methods of budding, grafting and cutting, performed by me in Fairport, N. Y., show that the distinguishing characteristics described in the preceding paragraphs and in the detailed specification that follows come true to form and are fully established and transmitted through succeeding propagations.

The accompanying picture of the new variety shows the shape, color and relative size of the different parts of the plant, and the absence of thorns on flowering branches.

Observations of the new variety for the specific purpose of compiling data for this application were made on sunny days during the early part of September 1955, on plants growing outdoors in Fairport, N. Y.

The color terminology used in describing the new variety is in accordance to Ridgway's Color Standard and Nomenclature (whenever plate number followed by the abbreviation "Ridg." is given), Horticultural Color Chart of the British Color Council (whenever plant number followed by the abbreviation "Hort." is given) and general meaning of Webster's dictionary (when plate number is absent). The Horticultural Color Chart is used where Ridgway's Color Standard does not quite describe the actual specimen, and vice versa.

The color of this new variety, like any other living plant, is effected by solar exposure, temperature, humidity, soil condition, relative duration of nocturnal and diurnal hours and other known and unknown factors, and, therefore, will undergo appreciable changes from time to time. But the changes in this variety is so slight that it shall not cross its general color boundary. The colors described in words in this specification of the new variety are those seen outdoors in good daylight by persons of normal eyesight. The colors on the accompanying drawing of this new variety are those seen in greenhouse in good daylight by an artist with normal eyesight. Whenever the outdoor and greenhouse colors do not agree, the color as seen outdoors is the correct color of the new variety.

The following is a detailed specification of the new variety:

(1) Parentage: A sport of Vierlanden.
(2) Classification: A mutant belonging to the recurrent or continuous blooming variety of the cultivated species of the genus Rosa (botanic); a rose plant of the hybrid-tea class (commercial).
(3) Blooming habit: Recurrent, continuous.
(4) Quantity of blooms: Abundant outdoors.
(5) Flowering bud:
*Size.*—Large.
*Shape.*—Ovoid.
*Color of visible petal when sepals first begin to divide.*—Rose Bengal (Plate No. 25 "Hort.").
*Color of visible petal when sepals further divide.*—Rose Bengal (Plate No. 25/2 "Hort.").
*Color of visible petals when half blown.*—Rose Bengal (Plate No. 25/3 "Hort.").
*Peduncle.*—Smooth, long and Light Elm Green (Plate No. 17 "Ridg.").
*Sepals.*—Slightly serrated, very light green inside and Light Elm Green (Plate No. 17 "Ridg.") outside.
*Calyx.*—Large, smooth, Light Elm Green (Plate No. 17 "Ridg.") and frequently of a lighter shade of green.
*Opening characteristics.*—Opens up very well in most weather conditions as observed in Fairport, N. Y., during growing seasons.
(6) Flower:
*Size when fully opened.*—Five inches (average) in diameter.
*Quantity to a stem or flowering branch.*—One as a general rule, rarely in multiple.
*Form.*—High centered.
*Petalage.*—Double, normally exceeds 40 in number.
*Fragrance.*—A delightful mixture of sweet *Rosa centifolia* and *Rosa damascena* fragrances without the scent of tea.
*Lasting quality.*—Comparatively long, about that of hybrid tea roses named "Better Times" and "Briarcliff."
*Color.*—Rose Bengal (Plate No. 25/3 "Hort.") when almost fully or fully opened, with a small area of salmon-yellow (and sometimes light cream overcast with light yellow) at the base; excepting the small basal area, uniform coloring on all petals as a rule.
*Discoloration.*—As the bloom ages, discoloration takes place slowly, starting from Rose Bengal (Plate No. 25/3 "Hort.") changing gradually to lighter shades until it becomes very pale pink.
(7) Petals:
*Appearance.*—Satiny both sides.
*Shape.*—Ovoid (smaller petals); heart-shaped but without the "bay" or large indentation at the free end (large petals).
*Arrangement.*—Partly regular.
*Color.*—Rose Bengal (Plate No. 25/3 "Hort.") both surfaces (occasionally a slight difference due to light, temperature, soil, etc.), with a small area of salmon-yellow (and sometimes light cream overcast with light yellow) at the base.
*Persistence.*—Drops off cleanly in most weather conditions.
(8) Genital organs:
*Stigmas.*—Medium in size, Morocco Red (Plate No. 1 "Ridg.") or closely related red on the underside and the rim of orifice.
*Styles.*—Medium in size, uneven in height, light pink with streak of Morocco Red (Plate No. 1 "Ridg.") or closely related red.

*Pollens.*—Medium in quantity, Orange Yellow (Plate No. 3 "Ridg.") in color.
*Filaments.*—Medium in length, dull white or cream in color.
*Anthers.*—Medium in size, Orange Yellow (Plate No. 3 "Ridg.") in color, medium in quantity.
*Ovaries.*—All enclosed.
*Hips.*—Globular, smooth outer surface, medium orange color when mature.
*Chromosomes.*—Polyploid.
(9) Foliage:
*Form.*—A compound of three or five leaflets as a general rule.
*Texture.*—Leathery on both sides, with ordinary ribs and veins.
*Serrations.*—Evenly marked but not conspicuous, single form as a general rule.
*Stipules.*—A little wider and a little longer than those of the average hybrid tea rose.
*Color.*—Light Greenish Yellow (Plate No. 5 "Ridg.") on both surfaces, with an occasional light overcast of Oxblood Red (Plate No. 1 "Ridg.") on the tips and edges when young; Scheele's Green (Plate No. 6 "Ridg.") on both surfaces (occasionally the under surface being slightly lighter) when older but before maturity; Spinach Green (Plate No. 5 "Ridg.") on the upper side and Scheele's Green (Plate No. 6 "Ridg.") on the under side when mature.
*Quantity.*—About the same as that of Better Times.
(10) Wood or cane: smooth, well branched, Spinach Green (Plate No. 5 "Ridg.") in color.
(11) Thorns:
*Quantity.*—A dozen or less on the lower parts of an average bush, with practically no thorns on the upper canes or upper parts of the bush; averaging one or less thorn to a flowering branch; frequently just one or two thorns on the whole bush.
*Shape.*—Thin and wide base, with the end pointed slightly downward.
*Color.*—Dull light pink when young, buff and light brown when mature.
(12) Bush as a whole: Three and a half to four and a half feet at maturity when grown outdoors in ordinary garden soil in the region of Fairport, N. Y.; vigorous.
(13) Disease resistance: Very resistant to mildew and black spot fungi as observed in normal growing seasons in Fairport, N. Y.
(14) Hardiness: Hardy enough to survive with ease, without any artificial protection, the average winter in Fairport, N. Y., when grown in locations where the impacts of winter wind and morning sun are moderate, and drainage good.

I claim:

A new and distinct variety of rose plant substantially as hereinabove disclosed and described, characterized as to novelty by its similarity to its parent "Vierlanden" in respect to the size, shape, texture and growth habit of its canes and foliage, but greatly distinguished therefrom by the clear light pink color of its blooms as described, by the unusually small quantity of thorns (averaging one or less to a flowering branch), by its abundant production of blooms in outdoor gardens, by its great resistance to mildew and black-spot infections and by its sweet fragrance which is a combination of those of *Rosa centifolia* and *Rosa damascena,* but without the scent of tea.

No references cited.